United States Patent
Gamache et al.

(10) Patent No.: US 7,824,471 B2
(45) Date of Patent: Nov. 2, 2010

(54) CHROMATOGRAPHIC SYSTEMS AND METHODS FOR ELIMINATING INTERFERENCE FROM INTERFERING AGENTS

(75) Inventors: Yves Gamache, Adstock (CA); Andre Fortier, Adstock (CA)

(73) Assignee: Panalytique Inc., Quebec (CA)

( * ) Notice: Subject to any disclaimer, the term of this patent is extended or adjusted under 35 U.S.C. 154(b) by 193 days.

(21) Appl. No.: 12/090,717

(22) PCT Filed: Mar. 10, 2006

(86) PCT No.: PCT/CA2006/000364
§ 371 (c)(1),
(2), (4) Date: Jul. 23, 2008

(87) PCT Pub. No.: WO2007/045068
PCT Pub. Date: Apr. 26, 2007

(65) Prior Publication Data
US 2009/0165642 A1    Jul. 2, 2009

Related U.S. Application Data

(60) Provisional application No. 60/727,850, filed on Oct. 19, 2005.

(51) Int. Cl.
*B01D 53/02* (2006.01)
(52) U.S. Cl. .................. 95/82; 95/86; 96/101; 96/103; 96/104; 96/106; 73/23.35; 73/23.42
(58) Field of Classification Search ........... 95/82, 95/86, 88, 89; 96/101, 103, 104, 106; 73/23.35, 73/23.39, 23.41, 23.42
See application file for complete search history.

(56) References Cited

U.S. PATENT DOCUMENTS 3,524,305 A * 8/1970 Ives .................. 96/104

(Continued)

FOREIGN PATENT DOCUMENTS

EP         0 246 572 A1    11/1987

(Continued)

OTHER PUBLICATIONS

International Search Report (Form PCT/ISA/210) and Written Opinion of the International Searching Authority (Form PCT/ISA/237), for PCT/CA2006/000364, Jul. 10, 2006, 7 pages.

(Continued)

*Primary Examiner*—Michael A Marcheschi
*Assistant Examiner*—Robert A Clemente
(74) *Attorney, Agent, or Firm*—Daly, Crowley, Mofford & Durkee, LLP

(57) ABSTRACT

The present invention provides a chromatographic method for eliminating interference from interfering agents, coming from the gas sample itself or from the system material used to perform the impurities measurements, on impurities to be quantified in a gas sample. The method advantageously relies on the use of an additional valve and an additional sample loop particularly arranged in a G. C. system, and also on an additional supporting gas inlet operatively connected to the system through the additional sample loop for providing the system with a supporting gas comprising at least a predetermined portion of a predetermined active gas that will react with the unwanted interfering impurities, if any, or with the column material to cancel out unwanted active sites. Thus, the method of the present invention can advantageously be used in gas chromatographic systems to improve sensitivity thereof by acting on column separation material.

16 Claims, 7 Drawing Sheets

U.S. PATENT DOCUMENTS

| | | | |
|---|---|---|---|
| 3,714,421 | A | 1/1973 | Josias et al. |
| 4,851,683 | A | 7/1989 | Yang et al. |
| 5,135,549 | A | 8/1992 | Phillips et al. |
| 5,152,176 | A * | 10/1992 | Bryselbout et al. ......... 73/23.41 |
| 5,570,179 | A | 10/1996 | Weckstrom |
| 5,612,489 | A | 3/1997 | Ragsdale et al. |
| 6,043,881 | A | 3/2000 | Wegrzyn et al. |
| 6,341,520 | B1 | 1/2002 | Satoh et al. |
| 6,679,093 | B2 * | 1/2004 | Johnson et al. .............. 73/1.02 |
| 7,216,528 | B2 | 5/2007 | Gamache et al. |
| 7,451,634 | B2 * | 11/2008 | Gamache et al. ........... 73/23.42 |
| 2009/0132206 | A1 | 5/2009 | Gamache et al. |

FOREIGN PATENT DOCUMENTS

| | | |
|---|---|---|
| WO | WO 2006/089412 A | 8/2006 |
| WO | WO 2007/045068 | 4/2007 |
| WO | WO 2007/098586 A1 | 9/2007 |

OTHER PUBLICATIONS

Smid et al.;"Optical Emission Spectroscopy in HMDSO/$O_2$ RF Glow Discharge;" WDS'05 Proceedings of Contributed Papers, Part II; ISBN 80-86732-59-2; Jan. 1, 2005; pp. 408-413, 2005.

PCT International Search Report and Written Opinion of the ISA for PCT/CA2006/000364, Jul. 10, 2006; 7 pages.

Supplemental European Search Report of he ISA dated Nov. 25, 2008 for EP 06705316.5; 2 pages.

PCT International Preliminary Report on Patentability of the ISA dated Apr. 22, 2008 for PCT/CA2006/000364; 1 page.

European Official Communication dated Mar. 20, 2009 for European Application No. EP 06705316.5, based on PCT/CA2006/000364, 4 pages.

Response to EP Official Communication dated Mar. 20, 2009 for PCT App. No. PCT/CA2006/000364; filed on Dec. 23, 2009; 8 pages.

PCT International Search Report and Written Opinion of the ISA dated Jun. 8, 2007 for PCT/CA2007/000314.

PCT International Preliminary Report on Patentability of the ISA dated Sep. 2, 2008 for PCT/CA2007/000314.

Response to EP Official Communication dated Oct. 10, 2008 for EP07701832.3 based on PCT/CA2007/00314 and filed on Nov. 7, 2008; 4 pages.

Chinese Official Action (with English translation) dated Mar. 31, 2010, for CN 2007800071414; 5 pages.

Supplementary European Search Report for European Application No. EP 06705316, PCT/CA2006/000364, dated Nov. 25, 2008, 7 pages.

Verzele, et al., "Determination of traces of nitrogen and argon in oxygen by a simple gas chromatographic method", J. of Chromatography, vol. 209, 1981, pp. 455-457, XP002505132.

* cited by examiner

CHROMATOGRAPHIC SYSTEMS AND METHODS FOR ELIMINATING INTERFERENCE FROM INTERFERING AGENTS

CROSS REFERENCE TO RELATED APPLICATIONS

This application is a National Stage Application under 35 U.S.C. §371 of International Application number PCT/CA2006/000364 filed on Mar. 10, 2006 which, along with the subject National Stage Application, claims the benefit of U.S. Provisional Application No. 60/727,850, filed 19 Oct. 2005 under 35 U.S.C. §119(e).

FIELD OF THE INVENTION

The present invention generally relates to chromatographic systems and methods for fluid analytical systems for measuring impurities in a gas sample. It more particularly concerns an improved chromatographic system and an improved method for eliminating interference from interfering agents, coming from the gas sample itself or from the system material, on impurities to be quantified in the gas sample.

BACKGROUND OF THE INVENTION

In the identification and quantification of impurities in a gas sample, the gas chromatographic process is very useful and popular. In the air separation industries, semiconductor or the so called wafer fab industries, H2 and CO production, CO2 plants and many other processes, the process gas chromatograph (G.C.) is a common and widely used tool to qualify the final product or to control the production process.

A typical chromatographic configuration presently used in the art relies on a simple injection valve, a separation column, a detector, signal amplification and conditioning and, finally, an integration software for peak impurity area calculation and transformation in proper engineering unit.

However, many gas production processes use by-products of another process plant as "raw material input" for a particular gas production. Often, in this type of process, there are many impurities in the raw material.

An example of such process is found in one type of production of high purity H2 from a by-product of another process plant. Hydrogen is a by-product from the production of Sodium Chlorate used for paint production. In this Hydrogen by-product, there are many impurities. Typical impurities are CO2, CO, N2, CL2, H2S, Chloroform, Trichloroethane, Methylene Chloride, Mercaptans, as non limitative examples. In the final H2 product, there could be traces of some of these impurities. In the quality process control, a process gas chromatograph is used to measure impurities in the final H2. Typical impurities measured are O2, N2, Ar, CH4, CO, CO2 and total Hydrocarbons.

Typical chromatograph configurations generally use separation columns made of molecular sieves and various porous polymers. However, with such typical configurations, a problem arises from other impurities that are in the sample and interfere with the impurities to be quantified.

A sample trap could not be installed on the sample inlet line to eliminate the unwanted interfering impurities because such trap will also affect to some extent the impurities to be measured.

In this above-described particular case, the O2 peak is affected by the accumulation of some of the impurities in the separation column. These impurities, which are stopped in the column and define active sites, react with the O2 from the sample. As a result, the O2 peak disappears, leading to false measurements.

Another example of such problem is found when attempting to measure H2 and O2 in a C3 stream, i.e. Propylene 85-95%, Propane≈5-15%, H2 50-500 ppm. In this particular process plant, there is trace of TEAL, i.e. Triethylaluminium, which is a metal alkyl. It reacts violently with air turning it into Aluminium Oxide.

Here again, the O2 peak is affected. The TEAL is stopped by the process G.C. separation column and reacts with the O2 from the sample. The O2 peak decreases slowly to zero after a few injections. Again, in this particular case, a sample trap could not be used on the sample line since it affects some other impurities to be measured.

Another example of such problem is found in some CO production plants. CO at high pressure and temperature react with the Iron from the steel pipe used to carry it. This reaction generates Iron Pentacarbonyl or Fe(CO)5. The Fe(CO)5 also affects the O2 peak in process G.C. The Fe(CO)5 accumulates in the separation column and scavenges the O2 in the sample.

Another adverse effect of Fe(CO)5 on analytical systems was found when attempting to measure hydrocarbons with a FID (Flame Ionisation Detector). The Fe(CO)5 burning in the H2 flame is decomposed and generates Iron Oxide that plugs the FID jet. The FID becomes out of use after only a few days of operation and this with only a few ppm in the sample. CO will also react with Nickel found in some metal gaskets and fittings or filters of the system to generate Nickel Tetracarbonyl, i.e. Ni(CO)4. This metal carbonyl will do the same type of interference as the Fe(CO)5.

Again, in this case, a sample trap cannot be used on the sample line for the same reason cited above.

Also known in the art, there is U.S. Pat. No. 5,612,489 granted to Ragsdale et al. which describes a method to reduce the interference mainly caused by column packing. They suggest the use of a doped carrier gas. They give example with an Oxygen doped Helium carrier gas. So there is at any time some Oxygen amount flowing into the separation column and the detector. They typically dope the carrier gas with less than 10 ppm of O2. This method satisfies the active site that reacts with the impurity to be measured.

However, there is some drawback to this method. First, like any gas chromatograph, when a sample is injected, there is a sudden change in the flow of the carrier gas, and of course in the detector flow. This may result in a strong baseline upset interfering with some impurities to be measured, mainly at low level. In fact, the flow change is changing the dilution ratio when using a dilution scheme to dope the carrier gas. When using a pre-mixed carrier gas, upon injection, the sudden change in column pressure and flow changes the equilibrium of adsorption for O2 or any other reactive gas used to dope the carrier gas, thereby causing a change in the ratio of doping. This also results in baseline upset that may interfere with the impurities peaks of interest. This situation is even more evident at low sample impurity concentration where the need for larger sampling loop is generally required.

Furthermore, for some detectors like the high frequency discharge or plasma emission, the presence of O2 into the discharge zone could quench the ionization resulting in a lower detector response. This leads to some limitation in regards to the quantity of the doping agent. Thus, in case of a strong interfering agent, the above-described prior art method does not perform.

Therefore, it would be desirable to provide an improved chromatographic system and an improved chromatographic method for eliminating the interference problems described above that could be used in standard G.C. configurations. More particularly, it would be desirable to provide a method for eliminating interference from interfering agents, coming from the gas sample itself or from the system material, on the impurities to be quantified in the gas sample.

SUMMARY OF THE INVENTION

An object of the present invention is to provide an improved chromatographic method and an improved chromatographic system that satisfy the above mentioned needs.

Accordingly, there is provided a chromatographic method for eliminating interference from interfering agents on impurities to be quantified in a gas sample. The method comprises the steps of:

a) providing a chromatographic system having a first and a second sample loop, a first and a second separation column and a detector serially connected through a plurality of valves, the system being provided with a carrier gas, the gas sample and a supporting gas doped with a doping element;

b) providing the first sample loop with the gas sample for filling the first sample loop with a sample gas volume;

c) injecting the sample gas volume into the first separation column to substantially separate the gas sample into a plurality of baseline resolved impurities peaks;

d) operatively connecting the first separation column to the second separation column for a predetermined transferring period of time for transferring at least one of the baseline resolved impurities peaks into the second column;

e) isolating the second column from the first column after the predetermined transferring period of time;

f) providing the second sample loop with the supporting gas for filling the second sample loop with a supporting gas volume;

g) injecting the supporting gas volume into the first separation column for sweeping the first column with the supporting gas volume; and h) venting the first separation column outside the system through a vent line.

The above-described method of the present invention advantageously allows to eliminate interference from interfering agents coming from the gas sample itself or from the system material used to perform the impurities measurements on the impurities to be quantified in the gas sample.

Moreover, the above-described method of the present invention can advantageously be used for improving the sensitivity of typical G.C systems.

Preferably, in the above-described method, the carrier gas is a predetermined gas and the supporting gas comprises the predetermined gas.

Also preferably, the doping element comprises at least one of the impurities to be quantified.

In a further preferred embodiment of the method of the present invention, the method advantageously further comprises, before the step h), a step of operatively connecting the first separation column to the second separation column for providing the second separation column with the supporting gas volume to sweep the second separation column therewith.

BRIEF DESCRIPTION OF THE DRAWINGS

These and other objects and advantages of the invention will become apparent upon reading the detailed description and upon referring to the drawings in which.

Figure 1:
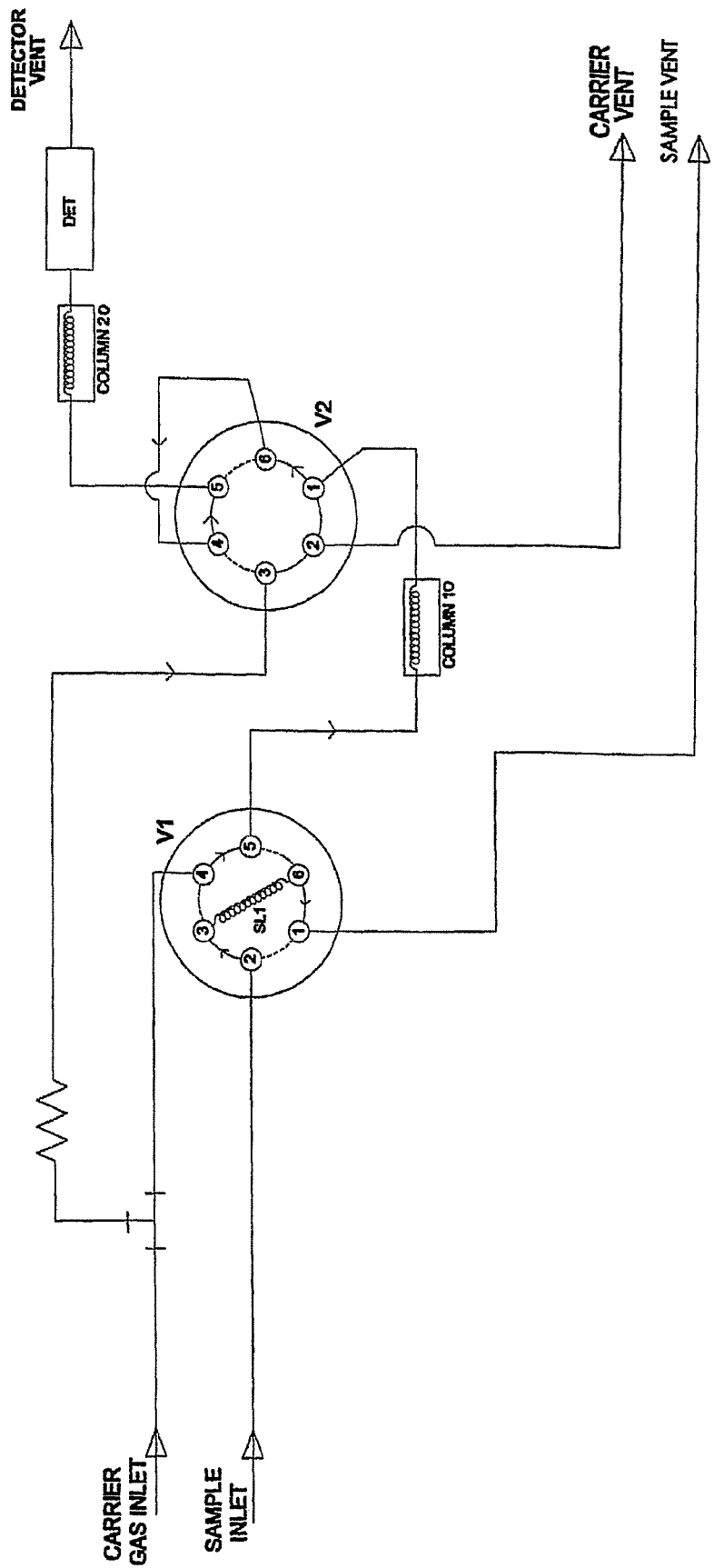
FIG. 1 (PRIOR ART) is a schematic representation of a typical analytical chromatographic system known in the art.

While the invention will be described in conjunction with example embodiments, it will be understood that it is not intended to limit the scope of the invention to such embodiments. On the contrary, it is intended to cover all alternatives, modifications and equivalents as may be included as defined by the appended claims.

DESCRIPTION OF PREFERRED EMBODIMENTS

In the following description, similar features in the drawings have been given similar reference numerals and in order to lighten the figures, some elements are not referred to in some figures if they were already identified in a preceding figure.

According to a first aspect, the present invention is directed to a method advantageously allowing to eliminate interference from some impurities present in a gas sample on impurities to be quantified in gas chromatographic systems.

According to a second aspect, the method of the present invention advantageously allows to eliminate interference from column or system material on impurities to be quantified in a gas sample. Thus, the method of the present invention can advantageously be used in gas chromatographic systems to improve sensitivity thereof by acting on column separation material, as it will be more clearly understood upon reading the following description.

As it will be more detailed thereinafter, the method of the present invention advantageously relies on the use of an additional valve and an additional sample loop particularly arranged in a G.C. system, and also on an additional supporting gas inlet operatively connected to the system through the additional sample loop for providing the system with a supporting gas comprising at least a predetermined portion of a predetermined active gas that will react with the unwanted interfering impurities, if any, or with the column material to cancel out unwanted active sites.

The method of the present invention will now be explained with an exemplary application. However, it should be understood that the method of the present invention is not limited to the components involved in this example and other component reactions could also be envisaged based on impurities and sample background involved in any particular application.

In some real cases in the field, the interfering agent is a volatile metal complex like Iron Pentacarbonyl $Fe(CO)_5$, Nickel Tetracarbonyl $Ni(CO)_4$ or Triethylaluminium. Such components are stopped by molecular sieve columns. So, they accumulate in it and affect $O_2$ of the gas sample to be measured by scavenging it.

Referring now to FIG. 1, there is shown a typical G.C. configuration of the prior art used to measure impurities in CO. As illustrated, there is one injection valve V1 to inject the sample volume SL1 and one venting valve V2 to vent out of the system the CO sample background. In this typical configuration, the first separation column 10 is used to get rid of the CO sample background while the second separation column 20, which is the analytical one, separates impurities like H2, O2, N2 and CH4 for example. The volatile metal will accumulate in the first separation column 10 and typically will react with O2 of the gas sample that oxidizes this metal complex. So the O2 impurities are removed from the sample and then cannot be measured by the system.

Figure 2:
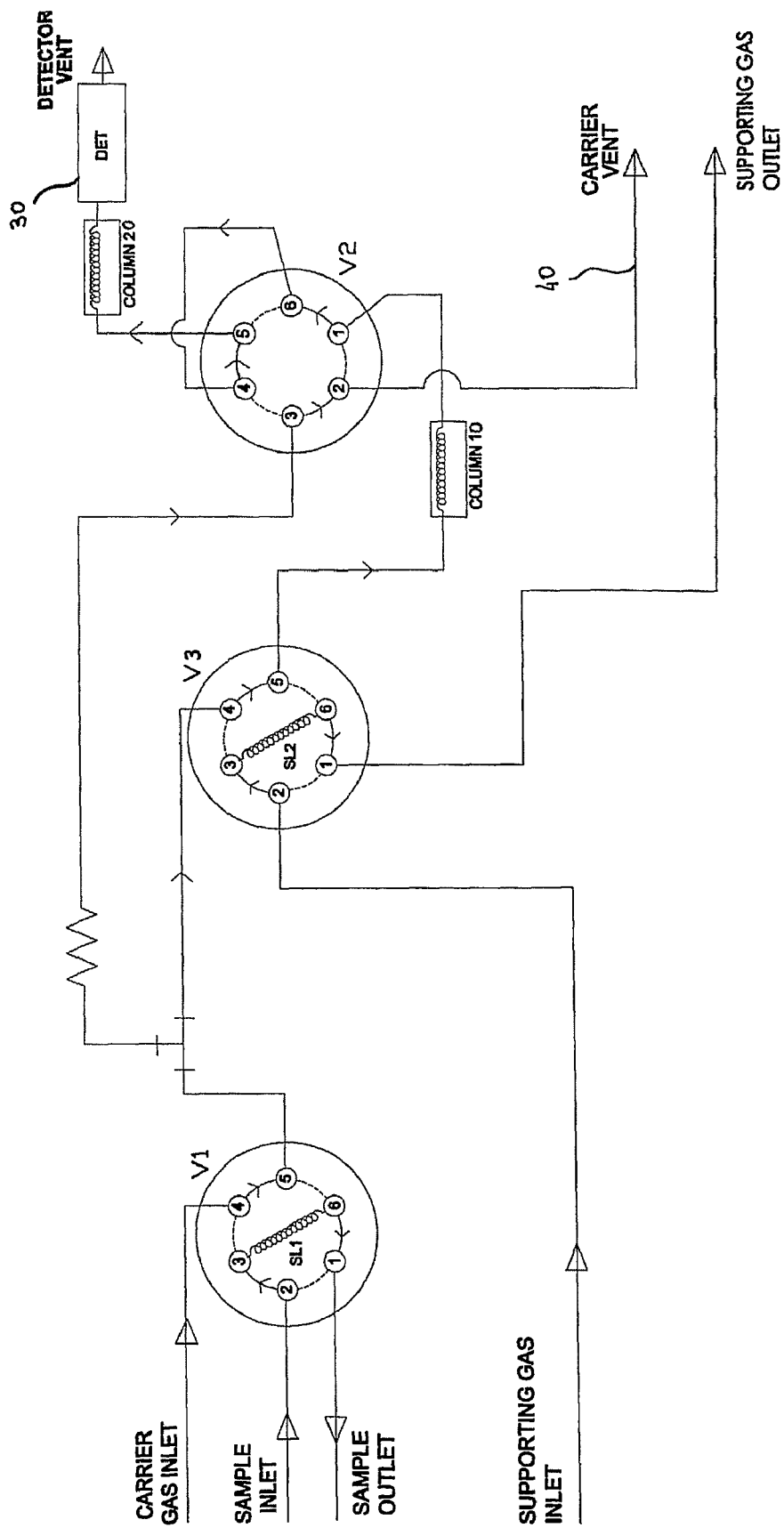
FIG. 2 is a schematic representation of an analytical chromatographic system, according to a preferred embodiment of the present invention, the system being in a first position.

Referring now to FIG. 2, there is shown an improved version of the system of FIG. 1 for fixing this problem, according to the present invention. In fact, as illustrated, the valve V3 and the sample loop SL2 have been added to the system of FIG. 1 for allowing to implement the method of the present invention. The implementation of the present method will now be described according to a particular example using oxygen but it is mentioned again that this example is not a limitative one and that other components than oxygen could also be envisaged. Indeed, since the metal complex is accumulating into the first separation column 10 and "eating" the O2, the idea is to supply the chromatographic system with an external source of O2 to completely oxidize the metal complex which has accumulated in the first separation column 10.

Still referring to FIG. 2, the chromatographic system used to implement the method of the present invention will now be described in more details. As illustrated, the chromatographic system has a first and a second sample loop SL1, SL2, a first and a second separation column 10, 20 and a detector 30 serially connected through a plurality of valves V1, V2, V3, three in the illustrated case. Preferably, each of the valves V1, V2, V3 is a three-way valve having independently actuated ports and providing a tight shut-off of the ports or a positive sealing action. For example, the diaphragm sealed valve of the same inventors which is described in U.S. patent application Ser. No. 11/064.501 entitled <<Diaphragm-sealed valve, analytical chromatographic system and method using the same>> is particularly well suited to implement the method of the present invention. It should however be mentioned that any other suitable valves could also be used. The system is provided with a carrier gas and the gas sample comprising the impurities to be quantified. The system is also provided with a supporting gas doped with a doping element. Preferably, the doping element, also called active gas, comprises at least one of the impurities to be quantified. More preferably, the supporting gas is doped with a predetermined concentration of the corresponding one of the impurities to be quantified. In other words, in the above-mentioned case wherein oxygen is to be measured in the gas sample, if the used carrier gas is Helium, then the supporting gas will be a mixture of O2 in Helium. The exact level of O2 is not critical as long as there is enough to completely oxidize the metal complex which has accumulated in the first separation column. A typical value we have used is 3% O2 in a balance gas of same type as carrier, but it should be understood that other values could also be envisaged. The carrier gas can be Helium, Argon or any other suitable gas, or even a mixture of them, as well known in the art. It is also worth mentioning that the doping element can also be any other active element that is not present in the gas sample to be analysed.

Figure 3:
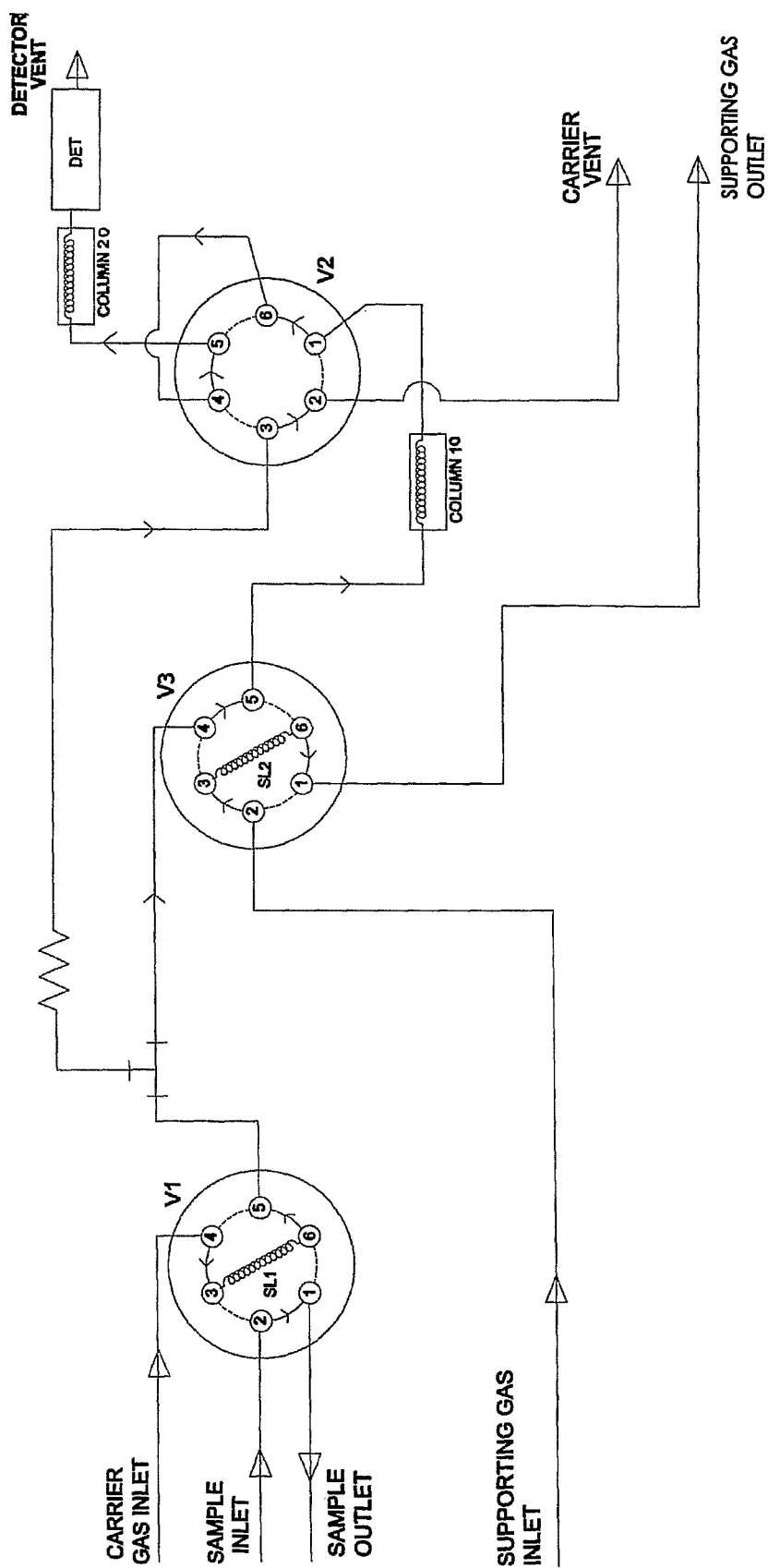
FIG. 3 is another schematic representation of the analytical chromatographic system shown in FIG. 2, the system being in a second position.
Figure 4:
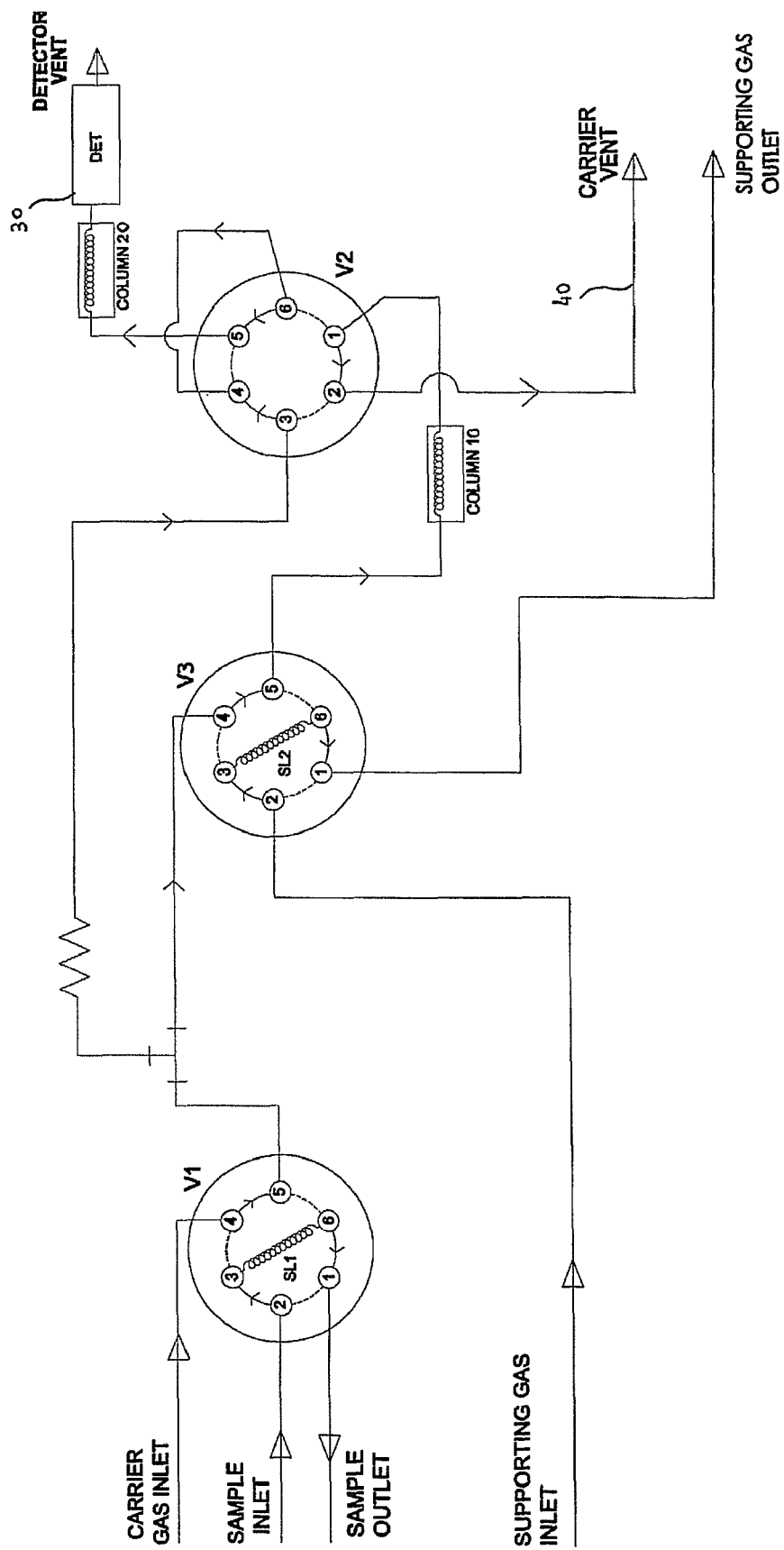
FIG. 4 is another schematic representation of the analytical chromatographic system shown in FIG. 2, the system being in a third position.

The chromatographic method of the present invention for eliminating interference from interfering agents on impurities to be quantified in a gas sample will now be described with reference to FIGS. 2 to 5 which show the system in different operating positions. Firstly, referring particularly to FIG. 2, the first sample loop SL1 is provided with the gas sample for filling the first sample loop SL1 with a sample gas volume. Referring now to FIG. 3, the valve V1 is then actuated for injecting the sample gas volume into the first separation column 10 to substantially separate the gas sample into a plurality of baseline resolved impurities peaks. In fact, the carrier gas carries the sample gas volume through the valve V3 and then into the first separation column 10 where the chromatographic separation process begins. Then, the first separation column 10 is operatively connected to the second separation column 20 for a predetermined transferring period of time for transferring at least one of the baseline resolved impurities peaks into the second separation column 20. Referring now to FIG. 4, when all impurities of interest have come out of the first separation column 10 and have been transferred into the second separation column 20, the second separation column 20 is isolated from the first column 10 after the predetermined transferring period of time. To do this, as illustrated, the valve V2 is actuated to advantageously vent the effluent of the column 10 outside the system. At this position, the unwanted sample background is evacuated out of the system. At the same time, the impurities of interest, which have been transferred into the second separation column 20, are separated into the second separation column 20 and individually integrated as a peak by the detector 30 and associated electronic and software (not shown). It should be noted that the impurities and sample background of the gas sample are not retained in the first separation column 10 but the metal complex is.

Figure 5:
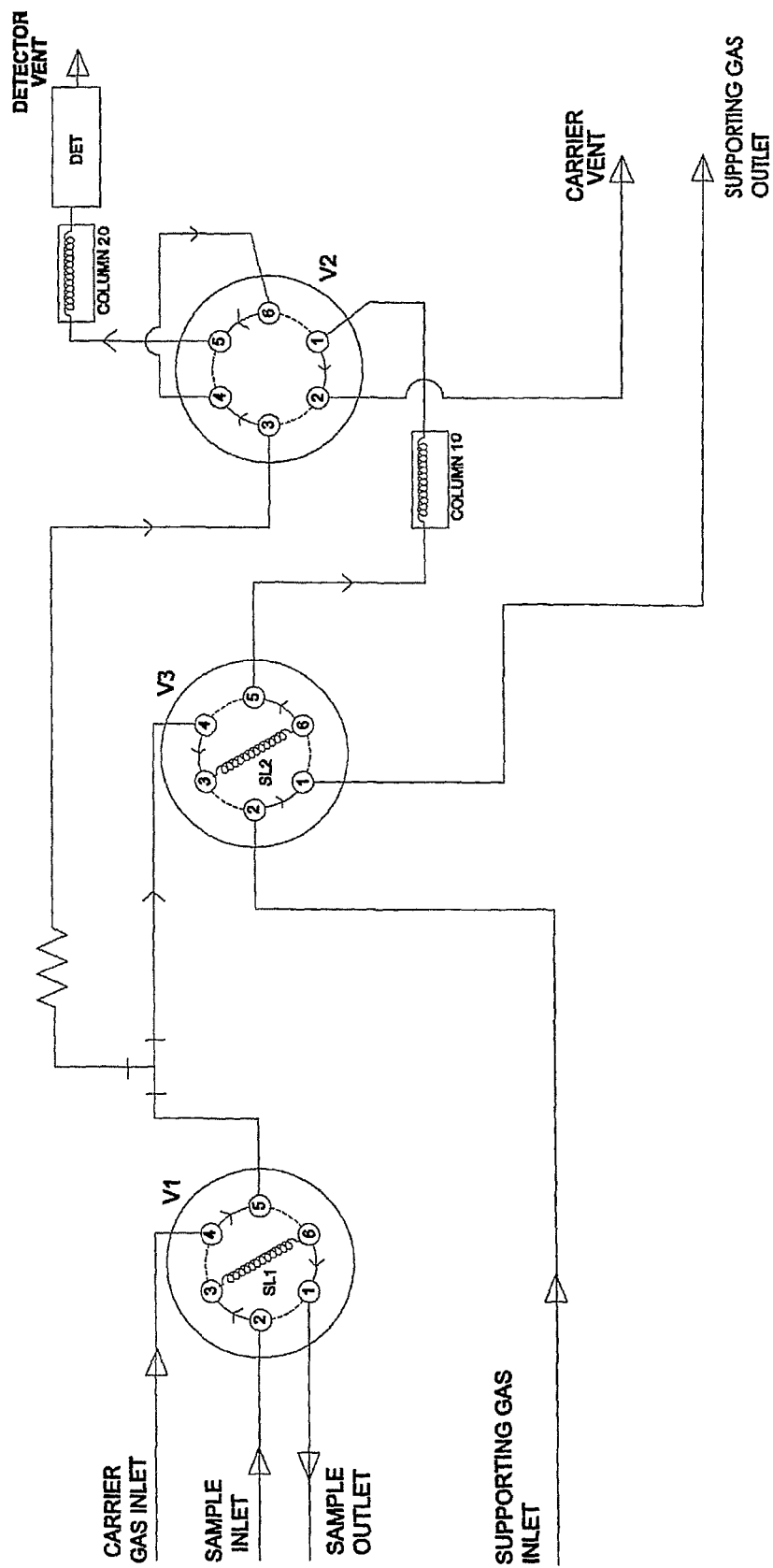
FIG. 5 is another schematic representation of the analytical chromatographic system shown in FIG. 2, the system being in a fourth position.

Still referring to FIG. 4, the second sample loop SL2 is then provided with the supporting gas for filling the second sample loop SL2 with a supporting gas volume. In this particular described example, the supporting gas is 3% O2 in a balance gas of the same type of that of the carrier gas. As already mentioned, other values could also be envisaged and other suitable doping elements could be used. Referring now to FIG. 5, the supporting gas volume is now injected into the first separation column 10 for sweeping the first separation column 10 with the supporting gas volume, in order to oxidize the metal complex which has accumulated therein. To perform this injection, the valve V3 is actuated while the second separation column 20 is still isolated from the first separation column 10. Advantageously, during the isolation of the second separation column 20 from the first column 10, the second separation column 20 is provided with the carrier gas passing therethrough. In fact, the carrier gas is advantageously supplied to the second separation column 20 through the valves V1, V2 and V3.

Since the first separation column 10 is isolated from the second one, this first separation column 10 is then vented outside the system through a vent line 40. Thus, the excess of O2 that does not react with the metal complex accumulated into the first separation column 10 is vented away through the valve V2. As that time, the sample injection valve V1 has advantageously been returned to its sampling position, as shown in FIG. 2.

When the O2 has been completely evacuated of the system, the valve V2 is advantageously brought back to its original position like shown in FIG. 2 and the cycle can be repeated. The valve V3 is also advantageously set back to its original position, as shown in FIG. 2. It is however worth mentioning that the valves V3 and V1 are actuated for a time long enough for carrier gas to sweep away volume contained in SL1 or SL2 into the system.

It should be mentioned that before the step of operatively connecting the first separation column 10 to the second separation column 20 for transferring therein the impurities peaks of interest, one can envisage to implement an additional step of venting the first separation column 10 outside the system through the vent line 40 for a predetermined period of time for venting at least a portion of the gas sample. For specific applications, it can be very useful if one wants to implement a heartcut step to the present method.

Figure 6:
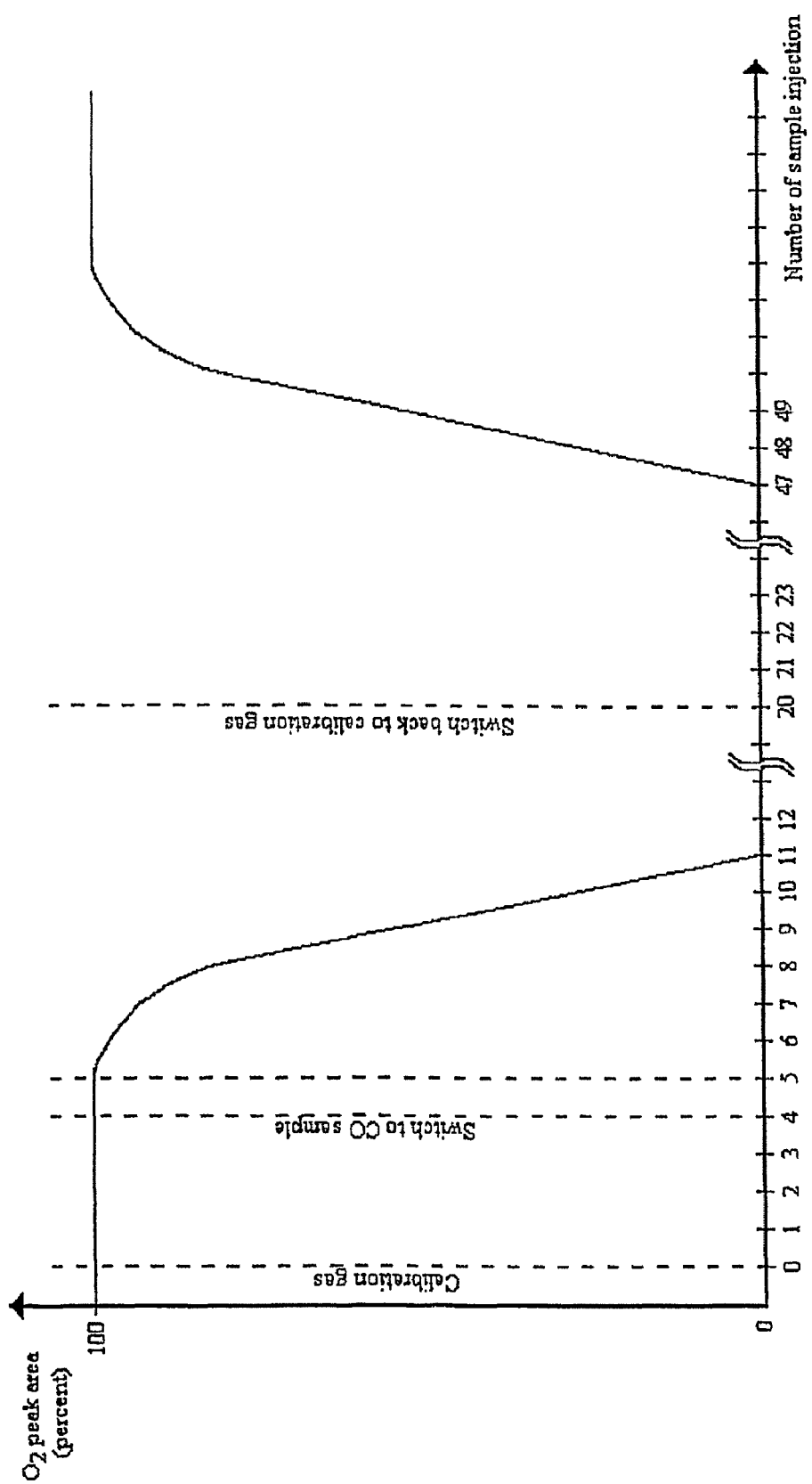
FIG. 6 (PRIOR ART) is a typical system response obtained with the analytical chromatographic system of FIG. 1.
Figure 7:
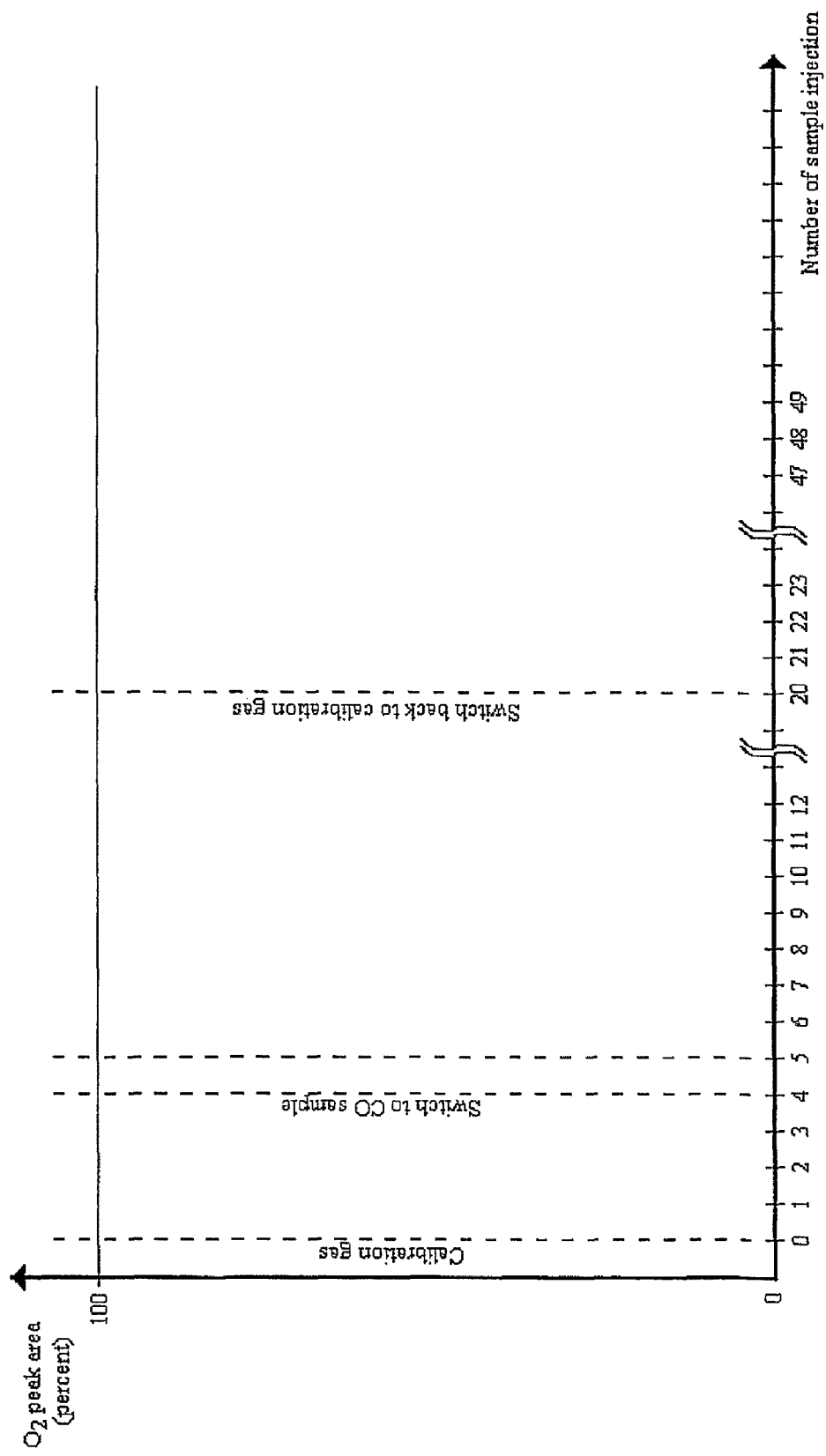
FIG. 7 is a typical system response obtained with the analytical chromatographic system of FIG. 2, according to the present invention.

To demonstrate the efficiency of the method of the present invention, for this particular exemplary case, reference is now made to FIGS. 6 and 7. FIG. 6 shows the response of O2 impurities obtained with the prior art configuration shown in FIG. 1, i.e. without using the valve V3 and the supporting gas. The graph shows O2 peak area in percentage versus the number of injection cycles. It can clearly be seen that after only 6 sample injections after switching on a CO sample, the O2 peak disappears. Furthermore, even after switching back to a clean calibration gas, the O2 peak does not come back. In fact, it takes many injections and several hours before recovering the O2 peak.

FIG. 7 shows the response of O2 impurities obtained with the configuration of the present invention illustrated through FIGS. 2 to 5, with the same test procedure. The result shows that the O2 peak, i.e. impurities to be measured, is no longer affected. Moreover, it has been proved that measurement results are repeatable and accurate.

Generally speaking, it is worth mentioning that other supporting gas chemistry could be used to react with other interfering agents of different nature that accumulate in the column material and react with the impurities to be measured.

It is worth mentioning that there are some interfering agents that, after reacting with the active gas in the supporting gas, may form a different chemical compound that is no longer retained in the separation column but rather vented out of the system. This is because the new generated chemical compound has no more affinity with the material of the separation column. In such case, the valve and tubing arrangement flow path could advantageously be made to backflush this new chemical compound out of the first separation column 10. This is to advantageously avoid that this compound travels all the way through the first separation column 10. One way or the other, in this particular case, the idea is to evacuate the new chemical compound out of the system by the shortest flow path. Any standard G.C. method referred to as "heartcut" or "backflush" could advantageously be used. These methods are well known by people involved in the art and therefore won't be further described.

As previously described, the general concept of this method is to eliminate active or reactive sites in the column material. The "activity" may be caused by unwanted impurities or by the column packing material itself. The later is a very important point when attempting to measure very low levels of impurities in a gas sample since chromatographic material itself may have some active sites that will adsorb some levels of impurities. By satisfying or filling these active sites, they are no longer available to react with the impurities to be measured in the gas sample. Doing so, this method has also a beneficial effect on the overall sensitivity of a particular system, even if the interference problem does not come from an external source.

In the preferred embodiment of the present method which has been described above, the so called doping or supporting gas never reaches the is detector 30 when there are impurities to be quantified. This advantageously prevents some of the problems of the prior art cited above from arising. However, other advantageous further embodiments could also be envisaged for a particular application. For example, one variation of the present method to advantageously help reduce column material activity will be to change timing of the valve V2 in order to allow some of the supporting gas to flow into the second separation column 20 to also reduce the analytical column activity for some impurities. It should nevertheless be noted that these various valve actuations are preferably done between chromatographic cycles to avoid any interference with the impurities to be quantified by the detector. Alternatively, before the step of venting the first separation column 10 outside the system, one can also envisaged to operatively connecting the first separation column 10 to the second separation column 20 for providing the second separation column 20 with the supporting gas volume to sweep the second separation column 20 therewith.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A chromatographic method for eliminating interference from interfering agents on impurities to be quantified in a gas sample, said method comprising the steps of:
    a) providing a chromatographic system having a first and a second sample loop, a first and a second separation column and a detector serially connected through a plurality of valves, said system being provided with a carrier gas, said gas sample and a supporting gas doped with a doping element;
    b) providing the first sample loop with said gas sample for filling said first sample loop with a sample gas volume;
    c) injecting said sample gas volume into said first separation column to substantially separate the gas sample into a plurality of baseline resolved impurities peaks;
    d) operatively connecting said first separation column to said second separation column for a predetermined transferring period of time for transferring at least one of said baseline resolved impurities peaks into said second column;
    e) isolating said second column from said first column after said predetermined transferring period of time;
    f) providing said second sample loop with said supporting gas for filling said second sample loop with a supporting gas volume;
    g) injecting said supporting gas volume into said first separation column for sweeping said first column with said supporting gas volume; and
    h) venting said first separation column outside the system through a vent line.

2. The chromatographic method according to claim 1, further comprising, before said step h), a step of operatively connecting said first separation column to said second separation column for providing the second separation column with said supporting gas volume to sweep said second separation column therewith.

3. The chromatographic method according to claim 1, further comprising, after said step g), a step of backflushing said first separation column.

4. The chromatographic method according to claim 1, further comprising, before said step d), a step of venting said first separation column outside the system through said vent line for a predetermined venting period of time for venting at least a portion of said gas sample.

5. The chromatographic method according to claim 1, further comprising a step of providing the second separation column with the carrier gas passing therethrough.

6. The chromatographic method according to claim 1, wherein each of said valves comprises a three-way valve having independently actuated ports and providing a tight shut-off of said ports.

7. The chromatographic method according to claim 1, wherein said carrier gas is a predetermined gas, said supporting gas comprising said predetermined gas.

8. The chromatographic method according to claim 7, wherein each of said carrier gas and said supporting gas comprises helium.

9. The chromatographic method according to claim 7, wherein each of said carrier gas and said supporting gas comprises argon.

10. The chromatographic method according to claim 1, wherein said doping element comprises at least one of said impurities to be quantified.

11. The chromatographic method according to claim 1, wherein said supporting gas comprises a predetermined concentration of the at least one of said impurities to be quantified.

12. The chromatographic method according to claim 1, wherein said supporting gas comprises about 3 percent of a corresponding one of said impurities to be quantified.

13. The chromatographic method according to claim 1, wherein said impurities to be quantified comprise oxygen, said doping element comprising oxygen.

14. The chromatographic method according to claim 1, wherein said interfering agents comprise a volatile metal complex.

15. The chromatographic method according to claim 14, wherein said interfering agents are selected from group consisting of Iron Pentacarbonyl, Nickel Tetracarbonyl and Triethylaluminium.

16. The chromatographic method according to claim 1, further comprising a step of providing the second separation column with the carrier gas passing therethrough, and wherein said carrier gas is a predetermined gas, said supporting gas comprising said predetermined gas, and said supporting gas comprising a predetermined concentration of the at least one of said impurities to be quantified.

* * * * *

UNITED STATES PATENT AND TRADEMARK OFFICE
CERTIFICATE OF CORRECTION

PATENT NO. : 7,824,471 B2  
APPLICATION NO. : 12/090717  
DATED : November 2, 2010  
INVENTOR(S) : Yves Gamache et al.

Page 1 of 1

It is certified that error appears in the above-identified patent and that said Letters Patent is hereby corrected as shown below:

Col. 1, line 39, delete "unit" and replace with --units--.

Col. 1, line 50, delete "non limitative" and replace with --non-limitative--.

Col. 2, line 7, delete "is trace" and replace with --is a trace--.

Col. 2, line 38, delete "give example" and replace with --give an example--.

Col. 3, line 12, delete "above mentioned" and replace with --above-mentioned--.

Col. 5, line 57, delete "of same" and replace with --of the same--.

Col. 5, lines 57-58, delete "as carrier," and replace with --as the carrier--.

Col. 6, lines 26 – 27, delete "electronic" and replace with --electronics--.

Col. 6, line 5, delete ". As" and replace with --. At--.

Col. 7, line 50, delete "later" and replace with --latter--.

Col. 8, line 9, delete "envisaged to" and replace with --envisage--.

Col. 10, line 11, delete "from group" and replace with --from a group--.

Signed and Sealed this  
Fourteenth Day of June, 2011

David J. Kappos  
*Director of the United States Patent and Trademark Office*